US00PP15989P2

(12) United States Plant Patent
MacKenzie

(10) Patent No.: US PP15,989 P2
(45) Date of Patent: Sep. 20, 2005

(54) ***HERNIARIA GLABRA* PLANT NAMED 'SEA FOAM'**

(50) Latin Name: *Herniaria glabra*
Varietal Denomination: Sea Foam

(76) Inventor: David S. MacKenzie, 14146 State Rd., Nunica, MI (US) 49448

( * ) Notice: Subject to any disclaimer, the term of this patent is extended or adjusted under 35 U.S.C. 154(b) by 90 days.

(21) Appl. No.: 10/895,000

(22) Filed: Jul. 20, 2004

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Penny J. Aguirre

(57) ABSTRACT

A new cultivar of *Hernaria glabra* or rupturewort plant named 'Sea Foam', characterized by green centered leaves that are edged in creamy yellow.

2 Drawing Sheets

Botanical classification: *Herniaria glabra.*
Variety denomination: 'Sea Foam'.

BACKGROUND OF THE INVENTION

The present invention relates to a new and distinct cultivar of rupturewort plant, botanically known as *Herniaria glabra* 'Sea Foam' and will be referred to hereinafter by its cultivar name, 'Sea Foam'.

'Sea Foam' originated as a naturally occuring branch sport (mutation) of an unnamed plant of the species, *Herniaria glabra* in Nunica, Mich. The original mutated parent plant, which led to 'Sea Foam' was growing in a nursery setting within a 60 square feet planting of the species *H. glabra*. The discoverer noticed a branch sport mutation with leaves edged in creamy yellow and later isolated the branch sport and named it 'Sea Foam'.

The species, *H. glabra*, typically displays all green leaves and tiny green flowers. 'Sea Foam' differs principally in having leaves that are green centered with broad margins of creamy yellow and creamy yellow flowers. The plant habit of 'Sea Foam' is similar to the parent species. There are no other known cultivars or varieties of this species known to the inventor.

The first successful asexual reproduction of 'Sea Foam' was carried out by its discoverer. This propagation took place under controlled conditions in Nunica, Mich. on Jun. 1, 2003. The mutated stem was excised, sectioned into two ⅜ inch long cuttings (bottom set of leaves removed from each), treated with 3000 ppm IBA, stuck in a porous organic growing medium in a 3¼ in. diameter pot, and placed under intermittent mist. Both cuttings formed roots in two weeks, survived, and were grown on to mature size. Once rooted, the plantlets took 2 months to fill a 3-inch diameter pot. At that point, the plants were planted into an outdoor growing bed where, during a 12 month period, they sprawl to a diameter of 1 foot across and continued to display leaves that were green centered and edged in creamy yellow, in contrast to the parent species which has leaves that are all green.

The characteristics of the cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Sea Foam' as a unique cultivar of *Herniaria glabra*.

1. Foliage is variegated with green centers and creamy yellow margins, while the species has foliage that is solid green in color.
2. Blooms during the month of July with tiny, apetalous, creamy yellow colored flowers that are crowded in axillary clusters. The species has green flowers.
3. Mature plants reach approximately 1 inch tall (measured from soil to top of the foliage) and 1 foot or more across (note: because the stems root as they spread, plants can potentially spread indefinitely).

BRIEF DESCRIPTION OF THE DRAWING

The accompanying photographic figures show typical foliage and growth habit of the new cultivar and the closest known comparison plant, the parent species *Herniaria glabra*. The plants in the photographs are one year old from cuttings. The colors depicted in the photographs are as accurate as possible with renditions of this type. The photographs were taken outdoors at 8:00 A.M. on Jun. 29, 2004 under hazy skies, in Nunica, Mich. They were photographed with a Nikon digital camera using no filters.

DETAILED BOTANICAL DESCRIPTION

Figure 1:
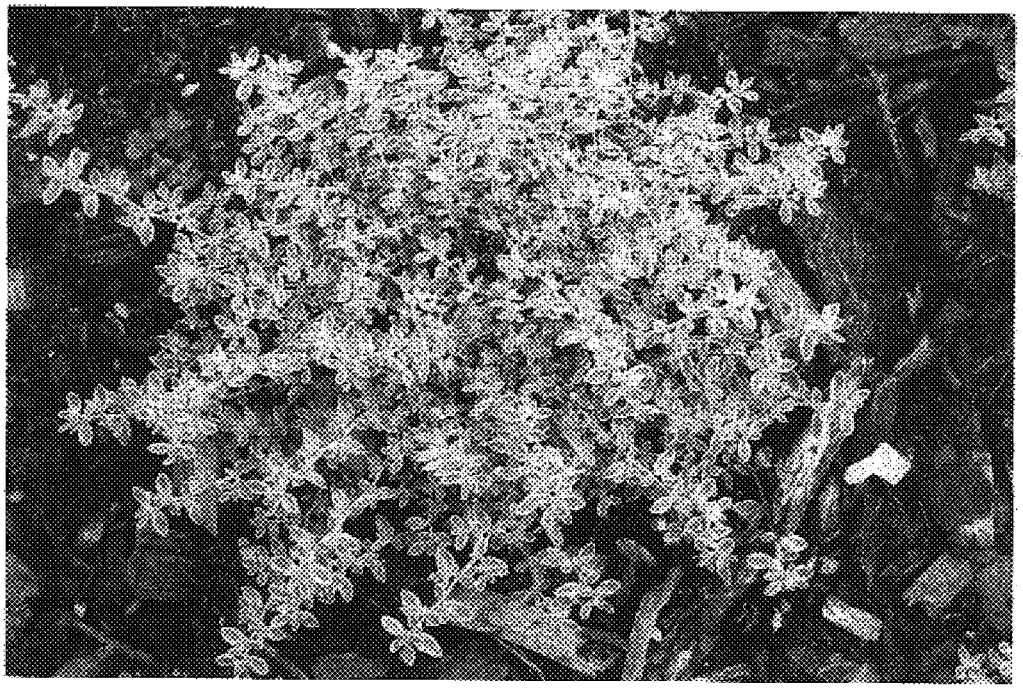
FIG. 1 is a perspective view of *Herniaria glabra* 'Sea Foam'.
Figure 2:
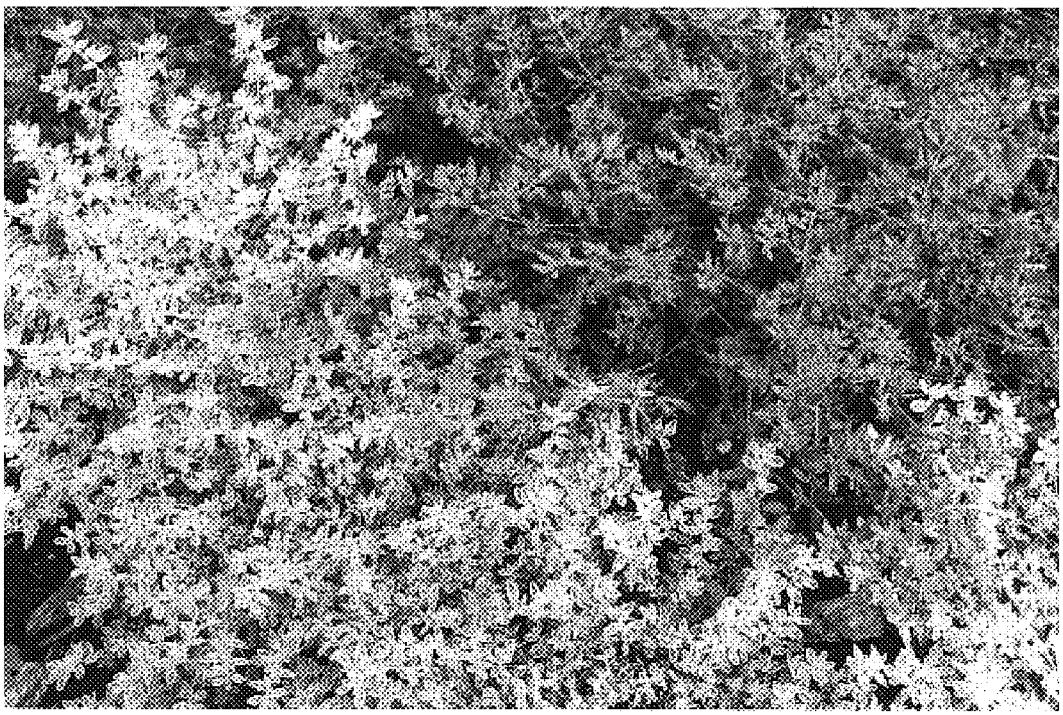
FIG. 2 is a perspective view of *Herniaria glabra* 'Sea Foam' in conjunction with the typical species *Herniaria glabra.*

'Sea Foam' has not been observed under all possible environmental conditions, and the phenotype my vary significantly with variations in environment; such as temperature, light intensity, and day length. The following observations, measurements, and comparisons describe this plant as grown in Nunica, Mich. when grown outdoors without cover under conditions that approximate those generally encountered in the home or commercial landscape.

The following traits have been repeatedly observed and are determined to be the basic characteristics of 'Sea Foam', which in combination distinguish this rupturewort as a new and distinct cultivar. The plants described are one year old, and have been grown in the ground in full sun conditions in Nunica, Mich. The color codes correspond to 1988 The Royal Horticultural Society Colour Chart. The following description is based upon one year-old plant that is mature in every respect.

1. The stems of 'Sea Foam' arise from the crown at 90 degree angles (to the earth) and immediately trail along the ground in horizontal fashion. They are characterized by a decumbent habit (meaning that they grow horizontally, in contact with the soil, but arch upward at their ends). Stems typically vary from 1 inch to 3 inches long and tend to branch with new stems arising from leaf nodes at 45 degree angles. Stems tend to root as they contact the soil. Stems are cylindrical in cross section, non-pithy, smooth, 1/32 inch in diameter, and colored grayed-green 195-A.
2. The internode distance ranges from 1/4 inch to 3/8 inch long.
3. Nodes are slightly swollen, colored yellow green 145-B and are 1/16 inch wide.
4. Each leaf originates at a node. Leaves are evergreen and arranged in opposite pairs except toward the tips of the stems where they are arranged alternately. Each leaf is ovate-lanceolate in outline. Leaf blades are flattened, semisucculent, and attached to the nodes at their bases, which are cuneate, and lack pedicles. Leaf apexes are acute.
5. Each leaf ranges from 1/8 to 1/4 inch long and from 1/8 to 3/16 inch wide. They are smooth on both sides with entire margins. Leaf blades are variegated with oval-shaped green centers surrounded by creamy yellow margins. On the upper surface, the green centers are green 136-C and range from 3/16 to 5/16 inch long by 3/32 to 5/32 inch wide. and the creamy yellow margins are colored yellow 12-D and range from 1/32 to 1/16 inch wide. The intersection of the green centers and creamy yellow margins is a clean edge. On the lower surface, the green centers are green 135-D and the margins are colored yellow 12-D.
6. Venation is not visible, even with magnification. No midrib is evident.
7. 'Sea Foam' blooms during the month of July with tiny, apetalous flowers that are crowded in axillary clusters. Each flower is approximately 1/8 inch in diameter, composed of 4 or 5 sepals each 1/16 inch long, hairless, ovate, round based, with obtuse apexes. Sepals (upper and lower surface) are colored the same color as the leaf edges, yellow 12-D. Anthers number 2 to 5, and produce yellow 8-A grainy, moderately abundant pollen.
8. No seed formation has ever been observed in Michigan.
9. The general growth habit of 'Sea Foam' is decumbent (stems trail horizontally from the crown and ascend at their tips). Over time, the stems obtain enough mass to weigh them down so that they contact the soil, and after a few months they form roots at their nodes.

The process repeats itself over and over and plants progressively expand and have been observed to measure 1 foot across at ground level after one year.

10. Propagation is successfully achieved year-round by stem cuttings. Cuttings will root without the aid of rooting hormone and can simply be laid upon the soil surface under intermittent mist. Rooting takes 7 to 14 days.
11. Plants have remained disease and insect free to date. This may indicate resistance to crown rot, which is occasionally observed in the parent species, but disease resistance has not been scientifically verified.

I claim:

1. A new and distinct *Hernaria glabra* plant named Sea Foam, as herein described and illustrated.

* * * * *